United States Patent
Glauser

(10) Patent No.: US 8,956,640 B2
(45) Date of Patent: *Feb. 17, 2015

(54) BLOCK COPOLYMERS INCLUDING A METHOXYETHYL METHACRYLATE MIDBLOCK

(75) Inventor: Thierry Glauser, Redwood City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1862 days.

This patent is subject to a terminal disclaimer.

(21) Appl. No.: 11/480,023

(22) Filed: Jun. 29, 2006

(65) Prior Publication Data

US 2008/0003253 A1    Jan. 3, 2008

(51) Int. Cl.
| | |
|---|---|
| *A61K 31/74* | (2006.01) |
| *A61F 2/00* | (2006.01) |
| *C08F 2/00* | (2006.01) |
| *C08F 12/20* | (2006.01) |
| *C08F 14/18* | (2006.01) |
| *C08F 114/18* | (2006.01) |
| *C08G 85/00* | (2006.01) |
| *C08F 118/02* | (2006.01) |
| *C08F 293/00* | (2006.01) |
| *A61L 31/10* | (2006.01) |
| *A61L 31/14* | (2006.01) |
| *A61L 31/16* | (2006.01) |
| *C09D 153/00* | (2006.01) |

(52) U.S. Cl.
CPC ............ *C08F 293/005* (2013.01); *A61L 31/10* (2013.01); *A61L 31/148* (2013.01); *A61L 31/16* (2013.01); *C09D 153/00* (2013.01); *A61L 2300/00* (2013.01)
USPC ..................... 424/423; 424/78.18; 424/78.27; 526/72; 526/242; 526/319

(58) Field of Classification Search
None
See application file for complete search history.

(56) References Cited

U.S. PATENT DOCUMENTS

| | | | |
|---|---|---|---|
| 4,931,287 A | 6/1990 | Bae et al. | |
| 5,019,096 A | 5/1991 | Fox, Jr. et al. | |
| 5,163,952 A | 11/1992 | Froix | |
| 5,219,945 A * | 6/1993 | Dicker et al. | 525/276 |
| 5,258,020 A | 11/1993 | Froix | |
| 5,476,909 A * | 12/1995 | Kim et al. | 525/408 |
| 5,607,467 A | 3/1997 | Froix | |
| 5,616,338 A | 4/1997 | Fox, Jr. et al. | |
| 5,670,283 A * | 9/1997 | Kato et al. | 430/46.4 |
| 5,674,242 A | 10/1997 | Phan et al. | |
| 5,688,493 A * | 11/1997 | Sugawara et al. | 424/61 |
| 5,723,219 A | 3/1998 | Kolluri et al. | |
| 5,824,049 A | 10/1998 | Ragheb et al. | |
| 5,869,127 A | 2/1999 | Zhong | |
| 5,873,904 A | 2/1999 | Ragheb et al. | |
| 5,879,713 A | 3/1999 | Roth et al. | |
| 5,932,299 A | 8/1999 | Katoot | |
| 5,962,138 A | 10/1999 | Kolluri et al. | |
| 5,997,517 A | 12/1999 | Whitbourne | |
| 6,096,070 A | 8/2000 | Ragheb et al. | |
| 6,099,563 A | 8/2000 | Zhong | |
| 6,110,483 A | 8/2000 | Whitbourne et al. | |
| 6,117,176 A * | 9/2000 | Chen | 623/36 |
| 6,143,354 A | 11/2000 | Koulik et al. | |
| 6,159,978 A | 12/2000 | Myers et al. | |
| 6,179,817 B1 | 1/2001 | Zhong | |
| 6,180,632 B1 | 1/2001 | Myers et al. | |
| 6,197,051 B1 | 3/2001 | Zhong | |
| 6,214,901 B1 | 4/2001 | Chudzik et al. | |
| 6,231,590 B1 | 5/2001 | Slaikeu et al. | |
| 6,245,760 B1 | 6/2001 | He et al. | |
| 6,248,129 B1 | 6/2001 | Froix | |
| 6,258,371 B1 | 7/2001 | Koulik et al. | |
| 6,262,034 B1 | 7/2001 | Mathiowitz et al. | |
| 6,270,788 B1 | 8/2001 | Koulik et al. | |
| 6,277,449 B1 | 8/2001 | Kolluri et al. | |
| 6,299,604 B1 | 10/2001 | Ragheb et al. | |
| 6,306,176 B1 | 10/2001 | Whitbourne | |
| 6,344,035 B1 | 2/2002 | Chudzik et al. | |
| 6,383,509 B1 | 5/2002 | Donovan et al. | |
| 6,387,379 B1 | 5/2002 | Goldberg et al. | |
| 6,451,972 B1 * | 9/2002 | Scolastico et al. | 530/330 |
| 6,475,779 B2 | 11/2002 | Mathiowitz et al. | |
| 6,482,834 B2 | 11/2002 | Spada et al. | |
| 6,524,347 B1 | 2/2003 | Myers et al. | |
| 6,525,145 B2 * | 2/2003 | Gevaert et al. | 525/450 |
| 6,528,526 B1 | 3/2003 | Myers et al. | |
| 6,530,950 B1 | 3/2003 | Alvarado et al. | |
| 6,530,951 B1 | 3/2003 | Bates et al. | |

(Continued)

FOREIGN PATENT DOCUMENTS

| | | |
|---|---|---|
| EP | 1 275 670 | 1/2003 |
| JP | 2003-252940 | 9/2003 |

(Continued)

OTHER PUBLICATIONS

Blindt et al. Journal of the American College of Cardiology 2006 47:1786-1795.*

(Continued)

*Primary Examiner* — Juliet Switzer
*Assistant Examiner* — Caralynne Helm
(74) *Attorney, Agent, or Firm* — Squire Patton Boggs (US) LLP

(57) ABSTRACT

A block copolymer comprising a methoxyethyl methacrylate (MOEMA) midblock is provided for forming a coating a medical device for controlled release of a bioactive agent.

28 Claims, No Drawings

(56) References Cited

U.S. PATENT DOCUMENTS

| | | |
|---|---|---|
| 6,613,432 B2 | 9/2003 | Zamora et al. |
| 6,620,617 B2 | 9/2003 | Mathiowitz et al. |
| 6,663,662 B2 | 12/2003 | Pacetti et al. |
| 6,730,064 B2 | 5/2004 | Ragheb et al. |
| 6,776,796 B2 | 8/2004 | Falotico et al. |
| 6,790,228 B2 | 9/2004 | Hossainy et al. |
| 6,890,583 B2 | 5/2005 | Chudzik et al. |
| 7,005,137 B1 | 2/2006 | Hossainy et al. |
| 7,008,667 B2 | 3/2006 | Chudzik et al. |
| 7,077,859 B2 | 7/2006 | Sirhan et al. |
| 7,094,256 B1 | 8/2006 | Shah et al. |
| 8,153,036 B2 * | 4/2012 | Kurihara et al. .......... 264/5 |
| 2001/0007083 A1 | 7/2001 | Roorda |
| 2001/0029351 A1 | 10/2001 | Falotico et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0051730 A1 | 5/2002 | Bodnar et al. |
| 2002/0082679 A1 | 6/2002 | Sirhan et al. |
| 2002/0111590 A1 | 8/2002 | Davila et al. |
| 2002/0165608 A1 | 11/2002 | Llanos et al. |
| 2002/0176849 A1 | 11/2002 | Slepian |
| 2002/0188037 A1 | 12/2002 | Chudzik et al. |
| 2003/0004141 A1 | 1/2003 | Brown |
| 2003/0028243 A1 | 2/2003 | Bates et al. |
| 2003/0036794 A1 | 2/2003 | Ragheb et al. |
| 2003/0039689 A1 | 2/2003 | Chen et al. |
| 2003/0040790 A1 | 2/2003 | Furst |
| 2003/0060877 A1 | 3/2003 | Falotico et al. |
| 2003/0065377 A1 | 4/2003 | Davila et al. |
| 2003/0083739 A1 | 5/2003 | Cafferata |
| 2003/0225450 A1 * | 12/2003 | Shulze et al. .......... 623/1.15 |
| 2004/0034183 A1 * | 2/2004 | Kato et al. .......... 526/318 |
| 2005/0085592 A1 * | 4/2005 | Taniguchi et al. .......... 525/242 |
| 2005/0106203 A1 | 5/2005 | Roorda et al. |
| 2006/0095120 A1 * | 5/2006 | Herrmann .......... 623/1.44 |
| 2006/0105099 A1 * | 5/2006 | Takahashi et al. .......... 427/2.1 |

FOREIGN PATENT DOCUMENTS

| | | |
|---|---|---|
| WO | WO 02/47731 | 6/2002 |
| WO | WO 03/068836 | 11/2004 |

OTHER PUBLICATIONS

Slepian et al. Circulation 1998 97:1818-1827.*
Bates Science 1991 251:898-905.*
Lee et al. Pharmaceutical Research 2003 20: 264-269.*
U.S. Appl. No. 10/177,117, filed Jun. 21, 2002, Hossainy.
U.S. Appl. No. 10/177,154, filed Jun. 21, 2002, Hossainy et al.
U.S. Appl. No. 10/251,111, filed Sep. 19, 2002, Hossainy et al.
U.S. Appl. No. 10/376,348, filed Feb. 26, 2003, Ding et al.
U.S. Appl. No. 10/428,691, filed May 1, 2003, Pacetti.
U.S. Appl. No. 10/723,137, filed Nov. 25, 2003, Claude et al.
U.S. Appl. No. 11/483,304, filed Jul. 6, 2006, Glauser.
Reich, "DCC coupling of an alcohol to a carboxylic acid: carboxylic acid ester", downloaded www.syntheticpages.org/browse.php?&action=1&page Dec. 11, 2006, 2 pgs.
Riklin et al., "Improving enzyme-electrode contacts by redox modification of cofactors", Nature vol. 376, pp. 672-675 (1995).
Sung Chul Hong et al., "Preparation of Segmented Copolymers in the Presence of an Immobilized/Soluble Hybrid ATRP Catalyst System", Macromolecules 36, pp. 27-35 (2003).
Seong-Mu Jo et al., "New AB or ABA type block copolymers: atom transfer radical polymerization (ATRP) of methyl methacrylate using iodine-terminated PVDFs as (macro) initiators", Polymer Bulletin 44, 1-8 (2000).
Sehgal et al., "A Method for the High Efficiency of Water-Soluble Carbodiimide-Mediated Amidation", Analytical Biochemistry 218, pp. 87-91 (1994).
International Search Report for PCT/US2007/015097, filed Jun. 29, 2007, mailed Nov. 28, 2007, 13 pgs.
Han et al., "Synthesis of Thermally Sensitive Water-Soluble Polymethacrylates by Living Anionic Polymerizations of Oligo(ethylene glycol) Methyl Ether Methacrylates", Macromolecules 36, pp. 8312-8319 (2003).
Translation of Notice of Reasons for Rejection for appl. No. P2009-518285, dispatched Sep. 11, 2012, 3 pgs.

* cited by examiner

BLOCK COPOLYMERS INCLUDING A METHOXYETHYL METHACRYLATE MIDBLOCK

FIELD OF THE INVENTION

This invention generally relates to block copolymers that include a methoxyethyl methacrylate midblock, which is for coating an implantable device such as a drug eluting stent.

DESCRIPTION OF THE BACKGROUND

Blood vessel occlusions are commonly treated by mechanically enhancing blood flow in the affected vessels, such as by employing a stent. Stents are used not only for mechanical intervention but also as vehicles for providing biological therapy. To effect a controlled delivery of an active agent in stent medication, the stent can be coated with a biocompatible polymeric coating. The biocompatible polymeric coating can function either as a permeable layer or a carrier to allow a controlled delivery of the agent.

Although stents work well mechanically, the chronic issues of restenosis and, to a lesser extent, stent thrombosis remain. Pharmacological therapy in the form of a drug delivery stent appears to be a feasible means to tackle these issues. Polymeric coatings placed onto the stent serve to act both as the drug reservoir and to control the release of the drug. One of the commercially available polymer coated products is stents manufactured by Boston Scientific. For example, U.S. Pat. Nos. 5,869,127; 6,099,563; 6,179,817; and 6,197,051, assigned to Boston Scientific Corporation, describe various compositions for coating medical devices. These compositions provide to stents described therein an enhanced biocompatibility and may optionally include a bioactive agent. U.S. Pat. No. 6,231,590 to Scimed Life Systems, Inc., describes a coating composition, which includes a bioactive agent, a collagenous material, or a collagenous coating optionally containing or coated with other bioactive agents.

The nature of the coating polymers plays an important role in defining the surface properties of a coating. For example, the hydrophilicity/hydrophobicity of the coating polymer plays an important role in controlling the release of a drug. For instance, a hydrophobic coating can reduce water uptake of the coating so as to reduce the release rate of a drug in the coating meanwhile a hydrophilic coating can increase water uptake of the coating so as to increase the release rate of the drug.

Therefore, there is a need for polymeric materials which can be tailored to meet need of a coating on a medical device.

The polymer and methods of making the polymer disclosed herein address the above described problems.

SUMMARY OF THE INVENTION

Block copolymers by sequential polymerization of polymer blocks from different monomers are provided herein. The block copolymers have a good control of molecular weight and tailored physical and mechanical properties. These polymers can be used for controlled release of bioactive agents with diverse properties. For example, a block copolymer described herein can be used to form a coating on an implantable device, which can optionally include a bioactive agent.

The block copolymer described herein can be tailored to possess a variety of physical and mechanical properties. For example, the block copolymer can be an amphiphilic copolymer comprising hydrophobic and hydrophilic blocks. When the polymer is used for forming coating a medical device, phase separation can occur, yielding a homogeneous coating on the microscopic scale on the medical device. This phenomenon can be utilized to control the release of a drug or drugs. For example, a phase separated amphiphilic copolymer can host a hydrophobic drug in the copolymer's hydrophobic domains and a hydrophilic drug in the copolymer's hydrophilic domains so as to allow the simultaneous controlled release of bioactive agents with diverse properties. In some embodiments, an amphiphilic block copolymer can allow for the dissolution of a hydrophilic peptide in an organic solvent, which is important for forming a coating including the peptide by spray-coating.

A coating comprising a block copolymer described herein can include a bioactive agent. Some exemplary agents include, but are not limited to, paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), clobetasol, pimecrolimus, imatinib mesylate, midostaurin, prodrugs thereof, co-drugs thereof, or a combination thereof.

A medical device having the features described herein can be used to treat, prevent, or ameliorate a medical condition such as atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, urethra obstruction, tumor obstruction, and combinations thereof.

DETAILED DESCRIPTION

Block copolymers by sequential polymerization of polymer blocks from different monomers are provided herein. The block copolymers have a good control of molecular weight and tailored physical and mechanical properties. These polymers can be used for controlled release of bioactive agents with diverse properties. For example, a block copolymer described herein can be used to form a coating on an implantable device, which can optionally include a bioactive agent.

The block copolymer described herein can be tailored to possess a variety of physical and mechanical properties. For example, the block copolymer can be an amphiphilic copolymer comprising hydrophobic and hydrophilic blocks. When the polymer is used for forming coating a medical device, phase separation can occur, yielding a homogeneous coating on the microscopic scale on the medical device. This phenomenon can be utilized to control the release of a drug or drugs. For example, a phase separated amphiphilic copolymer can host a hydrophobic drug in the copolymer's hydrophobic domains and a hydrophilic drug in the copolymer's hydrophilic domains so as to allow the simultaneous controlled release of bioactive agents with diverse properties. In some embodiments, the hydrophobic drug can be any of paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), γ-hiridun, clobetasol, mometasone, pimecrolimus, imatinib mesylate, or midostaurin, or prodrugs, co-drugs, or combinations of these. In some embodiments, the hydrophilic drug can be a peptide (e.g., RGD, cRGD or mimetics thereof) or a drug carrying a charge.

In some embodiments, an amphiphilic block copolymer can allow for the dissolution of a hydrophilic peptide in an organic solvent, which is important for forming a coating including the peptide by spray-coating.

A medical device having a coating that includes the block copolymer having the features described herein can be used to treat, prevent, or ameliorate a medical condition such as atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, urethra obstruction, tumor obstruction, and combinations thereof.

In some embodiments, the block copolymer described herein can include a methoxyethyl methacrylate (MOEMA) midblock. Such a block copolymer can have a general formula of $$A\text{-}[MOEMA]_n\text{-}B \qquad \text{(Formula I)}$$

where A and B can be the same or different and n is a positive integer from about 1 to about 100,000, from about 10 to about 50,000, from about 100 to about 10,000, or from about 200 (e.g., 208) to about 500 (e.g., about 486). In some embodiments, the block copolymer can be formed via sequential incorporation or introduction of the different blocks. The midblock can include monomers other than MOEMA (non-MOEMA monomer). For example, monomers bearing a hydrophilic pendant group, such as a pendant hydroxyl group or amine group, can be copolymerized with MOEMA to form the midblock. Some examples of the monomers bearing a pendant hydroxyl group can be any hydroxylalkyl group such as hydroxyethyl methacrylate (HEMA), hydroxypropyl methacrylate (HPMA), hydroxyethyl acrylate (HEA), or hydroxypropyl acrylate (HPA). Some examples of monomers bearing an amino group can be any aminoalkyl group such as aminoethyl methacrylate (AEMA), aminopropyl methacrylate (APMA), aminoethyl acrylate (AEA), or aminopropyl acrylate (APA). In some embodiments, such non-MOEMA monomers can constitute up to 15 wt % of the midblock.

The pendant groups in the units in the midblock can be used to attach a bioactive agent. For example, a pendant group such as hydroxyl group or amino group can be used to attach a peptide, a drug, an active compound such as a nitric oxide generator, or a hydrophilic side chain such as poly(ethylene glycol) via established procedures, for example, via DCC coupling chemistry (see, e.g., Melanie Reich, SyntheticPage 129 (2001); D. Sehgal, I. K. Vijay, Anal. Biochem. 218:87 (1994); Riklin, et al., Nature, 376:672-675 (1995)).

In some embodiments, the MOEMA midblock can have different molecular weights. For example, the midblock can have a number average molecular weight ($M_n$) from about 10 kDa to about 140 kDa or from about 30 kDa to about 100 kDa (e.g., about 20 kDa, about 30 kDa, about 40 kDa, about 50 kDa, about 60 kDa, about 70 kDa, about 80 kDa, about 90 kDa or about 100 kDa). The end block(s) can have a number average molecular weight ($M_n$) from about 1 kDa to about 50 kDa or about 5 kDa to about 40 kDa (e.g., about 2 kDa, about 3 kDa, about 4 kDa, about 6 kDa, about 7 kDa, about 8 kDa, about 9 kDa, about 10 kDa, about 15 kDa, about 25 kDa, about 30 kDa, or about 40 kDa).

In some embodiments, the A and B blocks in Formula I can be formed from hydrophilic monomers and/or hydrophobic monomers. Both A and B blocks can comprise units derived from these monomers in a number from 1 to about 100,000, from about 10 to about 50,000, from about 50 to about 10,000, or from about 100 to about 500 (e.g., about 400). The hydrophobic monomers useful for forming the A or B block can be, for example, a vinyl monomer having a tertiary carbon having a general formula of $(R_1)(R_2)C=CH_2$ where $R_1$ and $R_2$ are non-hydrogen groups. In one embodiment, the hydrophobic monomer can be a methacrylate, or fluorinated methacrylate monomers. Alternatively, the hydrophobic monomers can be acrylate, or fluorinated acrylate monomers. As another alternative, the hydrophobic monomers can be 2-phenylacrylate or 2-phenylacrylamide. The ester group in these hydrophobic monomers can have a short chain alkyl group from C1 to C6. Examples of fluorinated methacrylate monomer are 1H,1H, 2H,2H-heptadecafluorodecyl methacrylate, and 1H,1H,3H-hexafluorobutyl methacrylate. The hydrophilic monomers can be any vinyl monomer having one or more hydrophilic groups, methacrylamide or acrylamide. Some examples of the hydrophilic groups are pyrrolidone group(s), carboxylic acid group(s), sulfone group(s), sulfonic acid group(s), amino group(s), alkoxy group(s), amide group(s), ester group(s), acetate group(s), poly(ethylene glycol) group(s), poly(propylene glycol) group(s), poly(tetramethylene glycol) group(s), poly(alkylene oxide) group(s), hydroxyl group(s), or a substituent that bears a charge and/or any of pyrrolidone group(s), carboxylic acid group(s), sulfone group(s), sulfonic acid group(s), amino group(s), alkoxy group(s), amide group(s), ester group(s), acetate group(s), poly(ethylene glycol) group(s), poly(propylene glycol) group(s), poly(tetramethylene glycol) group(s), poly(alkylene oxide) group(s), and hydroxyl group(s). Some exemplary hydrophilic monomers are vinyl pyrrolidone, hydroxyethyl methacrylate, hydroxypropyl methacrylate, methyl vinyl ether, alkyl vinyl ether, vinyl alcohol, methacrylic acid, acrylic acid, acrylamide, N-alkyl acrylamide, hydroxypropylmethacrylamide, vinyl acetate, 2-sulfoethyl methacrylate, 3-sulfopropyl acrylate, 3-sulfopropyl methacrylate, and PEG-methacrylate. Some exemplary substituents bearing a charge can be, for example, choline, phosphoryl choline, 2-aminoethyl methacrylate hydrochloride, N-(3-aminopropyl)methacrylamide hydrochloride, 2-N-morpholinoethyl methacrylate, vinylbenzoic acid, vinyl sulfonic acid, and styrene sulfonates.

The polymers described herein can be synthesized by atom transfer polymerization (ATRP) (Perrier, et al., Tetrahedron Lett 58 4053 (2002); Jo, et al., Polym Bull (Berlin) 44:1 (2002)). ATRP can be carried out in sequential steps to incorporate the different blocks (see, e.g., Hong et al., Macromolecules, 36(1):27-35 (2003)). For example, the polymer of Formula I can be prepared by (1) allowing an amount of monomers for block A to polymerize in the presence of an ATRP catalyst so as to make the A block, (2) causing an amount of monomers for the midblock to polymerize in the presence of the A block polymer and an ATRP catalyst to form a polymer comprising the A block and the midblock, and (3) causing an amount of monomers for the B block to polymerize in the presence of the polymer comprising the A block and the midblock and an ATRP catalyst to form the block copolymer of Formula I. The respective amounts of the monomers are determined by the respective molecular weight of the A, B and the midblock.

The sequence of forming the different blocks can vary and can be determined by one of ordinary skill in the art. Various ATRP catalysts are well documented. Generally, such catalysts comprise a metal complex. A preferred metal complex is a copper (I) catalyst.

In some embodiments, the block copolymer described herein can be synthesized using methods known in the art (see, for example, D. Braun, et al., Polymer Synthesis: Theory and Practice. Fundamentals, Methods, Experiments. 3$^{rd}$ Ed., Springer, 2001; Hans R. Kricheldorf, Handbook of Polymer Synthesis, Marcel Dekker Inc., 1992; G. Odian, Principles of Polymerization, 3$^{rd}$ ed. John Wiley & Sons, 1991). For example, free radical methods can be used to make the polymer (see, for example, D. Braun, et al., Polymer Synthesis: Theory and Practice. Fundamentals, Methods, Experiments. 3$^{rd}$ Ed., Springer, 2001; Hans R. Kricheldorf, Handbook of Polymer Synthesis, Marcel Dekker Inc., 1992).

Biocompatible Polymer

The block copolymer described above can be used to form coating on an implantable device, for example, a stent. The block copolymer can be used alone or in combination with another polymer. Such other polymers can be homopolymers or block or random copolymer. Such other polymers can be biodegradable (both bioerodable or bioabsorbable) or nondegradable. Representative biocompatible polymers include poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly (4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly (L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(trimethylene carbonate), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(iminocarbonate), polyurethanes, polyphosphazenes, silicones, polyesters, polyolefins, polyisobutylene and ethylene-alpha-olefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly (propylene fumarate), poly(n-butyl methacrylate), poly(sec-butyl methacrylate), poly(isobutyl methacrylate), poly(tert-butyl methacrylate), poly(n-propyl methacrylate), poly (isopropyl methacrylate), poly(ethyl methacrylate), poly (methyl methacrylate), polymers and co-polymers of hydroxyl bearing monomers such as HEMA, hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. PEO/PLA), polyalkylene oxides such as poly(ethylene oxide), poly(propylene oxide), poly(ether ester), polyalkylene oxalates, polyphosphazenes, polymers bearing pendant groups cu has phosphoryl choline or choline, poly(aspirin), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), biomolecules such as collagen, chitosan, alginate, fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, or combinations thereof. In some embodiments, the substrate coating described herein can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly (D,L-lactic acid), poly(L-lactic acid), poly(D,L-lactic acid-co-glycolic acid), or poly(L-lactic acid-co-glycolic acid), respectively.

In some embodiments, the substrate coating or basecoat preferably includes a fluoropolymer such as a Solef™ polymer (e.g., PVDF-HFP).

In some embodiments, the substrate coating can further include a biobeneficial material. The biobeneficial material can be polymeric or non-polymeric. The biobeneficial material is preferably substantially non-toxic, non-antigenic and non-immunogenic. A biobeneficial material is one that enhances the biocompatibility of a device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly (ether-esters) (e.g. PEO/PLA), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, phosphoryl choline, choline, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, PolyActive™, and combinations thereof. In some embodiments, the substrate coating can exclude any one of the aforementioned polymers.

The term PolyActive™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

In a preferred embodiment, the biobeneficial material can be a polyether such as poly (ethylene glycol) (PEG) or polyalkylene oxide.

Bioactive Agents

In some embodiments, the block copolymer described herein can be used, optionally with one or more bioactive agents, to form a coating on medical device. These bioactive agents can be any agent which is a therapeutic, prophylactic, or diagnostic agent. These agents can have anti-proliferative or anti-inflammatory properties or can have other properties such as antineoplastic, antiplatelet, anti-coagulant, anti-fibrin, antithrombonic, antimitotic, antibiotic, antiallergic, or antioxidant properties. Moreover, these agents can be cytostatic agents, agents that promote the healing of the endothelium, or agents that promote the attachment, migration and proliferation of endothelial cells while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules, which bind to complementary DNA to inhibit transcription, and ribozymes. Some other examples of bioactive agents include antibodies, receptor ligands, enzymes, adhesion peptides, blood clotting factors, inhibitors or clot dissolving agents, such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include 40-epi-(N1-tetrazolyl)-rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-1-oxy (4-amino-TEMPO), estradiol, anticancer agents, dietary supplements such as various vitamins, and a combination thereof. Examples of anti-inflammatory agents including steroidal and non-steroidal anti-inflammatory agents include biolimus, tacrolimus, dexamethasone, clobetasol, corticosteroids or combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, and genetically engineered epithelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by those of ordinary skill in the art.

Examples of Implantable Device

As used herein, an implantable device can be any suitable medical substrate that can be implanted in a human or veterinary patient. Examples of such implantable devices include self-expandable stents, balloon-expandable stents, stent-grafts, grafts (e.g., aortic grafts), heart valve prosthesis (e.g., artificial heart valves) or vascular graft, cerebrospinal fluid shunts, pacemaker electrodes, catheters, endocardial leads (e.g., FINELINE and ENDOTAK, available from Guidant Corporation, Santa Clara, Calif.), and devices facilitating anastomosis such as anastomotic connectors. The underlying structure of the device can be of virtually any design. The device can include a metallic material or an alloy such as, but not limited to, cobalt chromium alloy (ELGILOY), stainless steel (316 L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. The device can be, for example, a bioabsorbable stent.

Method of Use

In accordance with embodiments of the invention, a medical device as used herein can be, e.g., a stent. For a device including one or more active agents, the agent will retain on the device such as a stent during delivery and expansion of the device, and released at a desired rate and for a predetermined duration of time at the site of implantation.

Preferably, the device is a stent. The stent described herein is useful for a variety of medical procedures, including, by way of example, treatment of obstructions caused by tumors in the bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLE

A block copolymer described herein can be used to form a coating on a stent by spray-coating from a 2 wt % solution of the block copolymer in acetone/dimethylformamide (DMF) (4:1).

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A block copolymer comprising a methoxyethyl methacrylate (MOEMA) midblock and A and B end blocks, the copolymer having a general formula of A-[MOEMA]$_n$-B,
   wherein n is a positive integer from 1 to about 100,000,
   wherein the A block is formed from first monomer(s) and the B block is formed from second monomer(s), or the A block is formed from second monomer(s) and the B block is formed from first monomer(s),
   wherein the first monomer is selected from fluorinated methacrylate monomer(s), fluorinated acrylate monomer(s), 2-phenylacrylate, 2-phenylacrylamide, 1H,1H,2H,2H-heptadecafluorodecyl methacrylate, and 1H,1H,3H-hexafluorobutyl methacrylate,
   wherein the second monomer is selected from vinyl monomers having pendant groups selected from the group consisting of pyrrolidone group(s), carboxylic acid group(s), sulfone group(s), sulfonic acid group(s), amino group(s), alkoxy group(s), amide group(s), acetate group(s), poly(ethylene glycol) group(s), poly(propylene glycol) group(s), poly(tetramethylene glycol) group(s), poly(alkylene oxide) group(s), hydroxyl group(s), or a substituent that bears a charge or any of pyrrolidone group(s), carboxylic acid group(s), sulfone group(s), sulfonic acid group(s), amino group(s), alkoxy group(s), amide group(s), acetate group(s), poly(ethylene glycol) group(s), poly(propylene glycol) group(s), poly(tetramethylene glycol) group(s), poly(alkylene oxide) group(s), and hydroxyl group(s), and
   wherein the block copolymer is a phase separate amphiphilic copolymer.

2. The block copolymer of claim 1, wherein the midblock has a number average molecular weight ($M_n$) from about 30 kDa to about 100 kDa.

3. The block copolymer of claim 1, wherein the A and B end blocks independently have a number average molecular weight ($M_n$) from about 5 kDa to about 40 kDa.

4. The block copolymer of claim 1, wherein the midblock further comprises units of monomers having a hydrophilic pendant group.

5. The block copolymer of claim 4, wherein the units of monomers having a hydrophilic pendant group comprise up to about 15 wt % of the midblock.

6. The block copolymer of claim 5, wherein the hydrophilic pendant group is a hydroxyl group or an amino group.

7. The block copolymer of claim 5, wherein the monomer having a hydrophilic pendant group is hydroxyethyl methacrylate (HEMA), hydroxylpropyl methacrylate (HPMA), hydroxyethyl acrylate (HEA), hydroxypropyl acrylate (HPA), aminoethyl methacrylate (AEMA), aminopropyl methacrylate (APMA), aminoethyl acrylate (AEA), or aminopropyl methacrylate (APMA).

8. The block copolymer of claim 6, further comprising a peptide, a drug, an active compound or a hydrophilic side chain attached to the midblock via the hydroxyl group or the amino group.

9. The block copolymer of claim 1, comprising a hydrophilic domain(s) and a hydrophobic domain(s).

10. A coating on a medical device comprising a block copolymer according to claim 1.

11. The coating of claim 10, further comprising a bioactive agent.

12. The coating of claim 10, further comprising a bioactive agent selected from paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), γ-hiridun, clobetasol, mometasone, pimecrolimus, imatinib mesylate, or midostaurin, or prodrugs, co-drugs, or combinations of these.

13. A coating comprising the block copolymer of claim 1 and further a hydrophilic drug and a hydrophobic drug,
   wherein the block copolymer is an amphiphilic copolymer comprising a hydrophilic domain(s) and a hydrophobic domain(s), and
   wherein the hydrophobic domain(s) hosts the hydrophobic drug and the hydrophilic domain(s) hosts the hydrophilic drug such that the coating provides simultaneous controlled release of the hydrophilic drug and the hydrophobic drug.

14. The coating of claim 13, wherein the hydrophilic drug is a peptide or a drug carrying a charge.

15. The coating of claim 14, wherein the hydrophilic drug is RGD, cRGD or combination of these.

16. The coating of claim 12, wherein the medical device is a stent.

17. The coating of claim 12, wherein the medical device is a bioabsorbable stent.

18. The coating of claim 13, wherein the medical device is a stent.

19. The coating of claim 13, wherein the medical device is a bioabsorbable stent.

20. A coating on a medical device comprising a block copolymer according to claim 1, wherein the midblock further comprises units of monomers having a hydrophilic pendant group.

21. The coating of claim 20, wherein the units of monomers having a hydrophilic pendant group comprise up to about 15 wt % of the midblock.

22. The coating of claim 21, wherein the hydrophilic pendant group is a hydroxyl group or an amino group.

23. The coating of claim 21, wherein the monomers having a hydrophilic pendant group are hydroxyethyl methacrylate (HEMA), hydroxylpropyl methacrylate (HPMA), hydroxyethyl acrylate (HEA), hydroxypropyl acrylate (HPA), aminoethyl methacrylate (AEMA), aminopropyl methacrylate (APMA), or aminoethyl acrylate (AEA) aminopropyl methacrylate (APMA).

24. The coating of claim 22, further comprising a peptide, a drug, an active compound or a hydrophilic side chain attached to the midblock via the hydroxyl group or the amino group.

25. The block copolymer of claim 1, wherein the second monomer is selected from vinyl pyrrolidone, hydroxyethyl methacrylate, hydroxypropyl methacrylate, vinyl alcohol, methacrylic acid, acrylic acid, acrylamide, N-alkyl acrylamide, hydroxypropylmethacrylamide, 2-sulfoethyl methacrylate, 3-sulfopropyl acrylate, 3-sulfopropyl methacrylate, PEG-methacrylate, 2-N-morpholinoethyl methacrylate, vinylbenzoic acid, vinyl sulfonic acid, and styrene sulfonates.

26. The block copolymer of claim 1, wherein the substituent bearing a charge is choline or phosphoryl choline.

27. A block copolymer comprising a methoxyethyl methacrylate (MOEMA) midblock and A and B end blocks, the copolymer having a general formula of A-[MOEMA]$_n$-B,
   wherein n is a positive integer from 1 to about 100,000,
   wherein the A block is formed from first monomer(s) and the B block is formed from second monomer(s), or the A block is formed from second monomer(s) and the B block is formed from first monomer(s),
   wherein the first monomer is selected from vinyl monomers having a tertiary carbon having a general formula of $(R_1)(R_2)C=CH_2$ where $R_1$ and $R_2$ are non-hydrogen groups, fluorinated methacrylate monomer(s), fluorinated acrylate monomer(s), 2-phenylacrylate, 2-phenylacrylamide, 1H,1H,2H,2H-heptadecafluorodecyl methacrylate, and 1H,1H,3H-hexafluorobutyl methacrylate,
   wherein the second monomer is selected from vinyl pyrrolidone, hydroxyethyl methacrylate, hydroxypropyl methacrylate, vinyl alcohol, methacrylic acid, acrylic acid, acrylamide, N-alkyl acrylamide, hydroxypropylmethacrylamide, 2-sulfoethyl methacrylate, 3-sulfopropyl acrylate, 3-sulfopropyl methacrylate, PEG-methacrylate, 2-N-morpholinoethyl methacrylate, vinylbenzoic acid, vinyl sulfonic acid, and styrene sulfonates;
   wherein the block copolymer is a phase separate amphiphilic copolymer.

28. A method of treating or ameliorating a medical condition, comprising implanting in a human being a medical device comprising the coating of claim 10, wherein the medical condition is selected from atherosclerosis, restenosis, vascular dissection or perforation, vascular aneurysm, vulnerable plaque, chronic total occlusion, claudication, anastomotic proliferation for vein and artificial grafts, bile duct obstruction, urethra obstruction, tumor obstruction, diabetic vascular disease, and combinations thereof.

* * * * *